US00PP12943P2

(12) United States Plant Patent
Zaiger et al.

(10) Patent No.: US PP12,943 P2
(45) Date of Patent: Sep. 10, 2002

(54) INTERSPECIFIC TREE NAMED 'CRIMSON HEART'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 26 days.

(21) Appl. No.: 09/833,261

(22) Filed: Apr. 10, 2001

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following unique combination of features that are desirable in a new variety:

1. Heavy and regular production of large, red flesh, clingstone fruit.
2. Fruit with very good flavor and eating quality.
3. Fruit with firm flesh, good storage and shipping quality.
4. Fruit with a good balance between sugar and acid having high soluble solids of 15.5° Brix.

1 Drawing Sheet

BACKGROUND OF THE VARIETY

In the field of plant genetics, we conduct an extensive and continuing plant-breeding program including the organization and asexual reproduction of orchard trees, and of which plums, peaches, nectarines, apricots, cherries and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of plums and interspecific trees which are known to us, and mentioned herein, 'Laroda' Plum (non-patented), 'Queen Ann' Plum (non-patented), 'Friar' Plum (non-patented), interspecific trees 'Plum Parfait' (U.S. Plant Pat. No. 4,338), and 'Flavorosa' (U.S. Plant Pat. No. 10,285).

ORIGIN OF THE VARIETY

The present new and distinct interspecific tree [(*Prunus salicina*×(*Prunus salicina*×(*Prunus salicina*×*Prunus armeniaca*))×(*Prunus salicina*×*Prunus armeniaca*))×(*Prunus salicina*×*Prunus armeniaca*)] was originated by us in our experimental orchard as a first generation cross between the seedling 59EF110 and 'Plum Parfait' Plumcot (U.S. Plant Pat. No. 4,338). The seedling (59EF110) originated from a cross between two seedlings, one seedling originated from a cross of 'Laroda' Plum (non-patented) with 'Queen Ann' Plum (non-patented). The second seedling originated from crossing two seedlings, the first cross made with a seedling selected from an open pollinated 'Friar' Plum (non-patented) with a plumcot and, from this cross a seedling was selected and back crossed to the same plumcot. The plumcot originated from an open pollinated 'Red Beaut' Plum (U.S. Plant Pat. No. 2,539) seed. We planted and maintained a large group of these first generation crosses, growing on their own root, under close observation, during which time the present new seedling exhibited distinct and desirable fruit characteristics and was selected in 1995 for asexual propagation and commercialization.

ASEXUAL REPRODUCTION OF THE VARIETY

Asexual reproduction of the distinct variety of interspecific tree was by budding to 'Nemaguard' Rootstock (non-patented), a standard rootstock for interspecific trees in California, as performed by us in our experimental orchard near Modesto, Calif., and shows that reproductions run true to the original tree and all characteristics of the tree and its fruit are established and transmitted through succeeding asexual propagations.

SUMMARY OF THE VARIETY

The present distinct variety of interspecific tree [(Plum×(Plum×Plumcot)×(Plumcot))×(Plumcot)] is of large size, vigorous, upright in growth and a productive and regular bearer of large, firm, clingstone fruit with very good flavor and eating quality. The fruit is further characterized by having an attractive red flesh, holding firm on the tree 10 days after maturity, having good storage and shipping quality and having high soluble solids of 15.5° Brix with a good balance between sugar and acid. In comparison to the Plumcot 'Plum Parfait' (U.S. Plant Pat. No. 4,338), the present variety has larger leaves, has plum like fruit with no pubescence, which is larger in size and approximately one week earlier in maturity. In comparison to the interspecific tree 'Flavorosa' (U.S. Plant Pat. No. 10,285) the new variety has a higher winter chilling requirement, blooming 1 week later in the spring, the fruit is more round in shape and is 7 to 10 days later in maturity.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as true as is reasonably possible in a color representation of this type.

DESCRIPTION OF THE VARIETY

The following is a detailed botanical description of the present variety of interspecific tree, its flowers, foliage and fruit, as based on observations of 5 year old specimens budded on 'Nemaguard' Rootstock (non-patented) and grown near Modesto, Calif., with color terminology (except those in common terms) in accordance with Reinhold Color Atlas by A. Kornerup and J. H. Wanscher.

Tree:

*Size.*—Large. Pruned 10 to 12 feet in height and width, primarily for economical harvesting of fruit.

*Vigor.*—Vigorous. Tree growth of 5 to 6 feet in height and 4 to 5 feet in width the first growing season. Varies with type of soil and cultural practices.

*Growth.*—Upright growth habit. Heavy production tends to spread tree at bearing age.

*Branching habit.*—New growth upright. Crotch angle 25 to 30 degrees, spreading increases with weight of fruit.

*Productivity.*—Productive. Usually sets 2 or more times desired fruit for marketable crop load. Thinning and spacing of fruit necessary.

*Bearer.*—Has set full crop load 4 consecutive years. No alternate bearing observed.

*Density.*—Medium dense. Center branches removed to open tree to vase shape for improved sun light throughout the tree, which enhances growth of fruitwood and brix of fruit.

*Hardiness.*—Hardy for all stone fruit growing areas of California, grown in USDA Hardiness Zone 9.

Trunk:

*Size.*—Large. Circumference — 21 inches, measured 9 inches above ground on a 5 year old tree. Varies with soil type, climatic conditions and cultural practices.

*Stocky.*—Medium. Varies slightly with type and fertility of soil.

*Surface texture.*—Medium rough. Roughness increases with age of tree.

*Color.*—Varies from grayish brown to brown (7-D-2) to (7-E-4).

Branches:

*Size.*—Medium. Circumference — 8 inches, measured 48 inches above ground on a 5 year old tree.

*Surface texture.*—Varies from smooth on new growth to medium rough. Roughness increases with age.

*Lenticels.*—Numerous, average 65 in 4 square inch surface. Average length 3/32 inch, increases in size as branch grows larger. Average width 3/64 inch. Color varies from grayish yellow to banana yellow (4-B-5) to (4-B-7).

*Color.*—One year old growth varies from olive green to light golden brown (2-F-6) to (6-B-6). Older growth varies from oak brown to bronze brown (5-D-6) to (5-E-5).

Leaves:

*Size.*—Large. Average length 4¼ inches. Average width 1¾ inches.

*Form.*—Oblanceolate.

*Apex.*—Acuminate.

*Base.*—Cuneate.

*Margin.*—Doubly serrate.

*Thickness.*—Medium.

*Surface texture.*—Upper surface varies from smooth to lightly indented over veins, glabrous. Lower surface relatively smooth except for small ridges of midrib and pinnate venation, glabrous.

*Petiole.*—Average length ½ inch. Average width 3/32 inch. Color — light olive green (29-D-6). Grooved longitudinally.

*Glands.*—Size — small. Average diameter 1/32 inch. Globose. Number — varies from 1 to 4, average number 3. Located on base of leaf blade and upper portion of petiole. Color — grayish yellow (3-B-7).

*Color.*—Upper Surface varies from deep green to dark green (29-F-7) to (29-F-8). Lower Surface varies from dull green to bracken green (29-D-6) to (29-E-7).

*Midvein.*—Pronounced, extends into petiole. Color — light olive green (29-D-6). Pinnate venation.

Flower buds:

*Size.*—Small. Average length — 9/32 inch. Average diameter — 3/16 inch. Four days before opening.

*Hardiness.*—Hardy in all stone fruit growing areas of California, grown in USDA Hardiness Zone 9.

*Pubescence.*—Wanting.

*Form.*—Plump, free, conical.

*Shape.*—Obtuse, becomes more elongated as bud matures.

*Color.*—White (29-A-1).

*Peduncle.*—Average length — 13/32 inch. Average width — 3/64 inch. Color — light green (29-B-7).

*Number of flower buds per spur.*—Average 17. Varies from 10 to 25.

Flowers:

*Size.*—Medium, non-showy. Average height — 15/32 inch. Average width — 47/64 inch.

*Color.*—White (29-A-1).

*Pistil.*—Normally one, varies from 1 to 2. Average length — 5/16 inch, stigma 1/16 inch below anthers. Color — white to yellowish white (1-A-1) to (1-A-2). Pubescence — wanting.

*Stamens.*—Number varies from 38 to 49 per flower. Average number — 43. Average filament length — 19/64 inch. Filament color — white to pale yellowish white (1-A-1) to (1-A-2). Anther color — light yellow to vivid yellow (3-A-6) to (3-A-8).

*Petal.*—Number — five, alternately positioned to sepals. Shape — elliptic, narrows at point of attachment. Size — medium. Average length — 25/64 inch. Average width — 11/32 inch. Color — white (29-A-1). Surface — smooth, edges of petals curved slightly toward center to form bowl shape around anthers and pistil. Margin varies from smooth to slightly scalloped.

*Sepals.*—Five. Triangular, apex slightly rounded. Alternately spaced between petals. Average length — 9/64 inch. Average width — 5/64 inch at point of attachment. Color — upper surface — grayish green in center to pistachio green near outer edges (28-C-5) to (28-C-4), glabrous. Lower surface — light green to grayish green to, glabrous. Varies with age of maturity.

*Pollen.*—Abundant, pollen sacs full. Color — light yellow to yellow (3-A-5) to (3-A-7).

*Pollenizer.*—Self-sterile, pollenizer required. Some of the factors affecting blooming dates that must be considered when selecting a pollenizer for specific areas. Winter chilling hours, number of heat units to excite bud initiation, type of rootstock, soil type, cultural practices and climatic conditions.

*Fragrance.*—Slight.

*Blooming period.*—Date of First Bloom Feb. 19, 2000. Date of Petal Fall Feb. 28, 2000. Varies slightly with climatic conditions.

*Number of flowers per bud.*—Average number 3. Varies from 1 to 4.

*Peduncle.*—Average length — 15/32 inch. Average width — 3/64 inch. Color — light green (29-B-7).

Fruit:

*Maturity when described.*—Firm ripe.

*Date of first picking.*—May 28, 2000.

*Date of last picking.*—Jun. 2, 2000. Varies slightly with climatic conditions.

*Form.*—Globose, nearly rounded, slightly retuse at apex and base on most fruit.

*Size.*—Large. Average diameter axially — 2¼ to 2⅜ inches. Average transversely in suture plane 2¼ to 2⅜ inches. Average weight 127.8 grams. Average weight varies with number fruit per tree, fertility of soil and climatic conditions.

*Suture.*—Very shallow, extends from base to apex.

*Ventral surface.*—Nearly smooth, very slightly lipped.

*Apex.*—Varies from nearly rounded to slightly retuse.

*Base.*—Varies from flat to slightly retuse.

*Cavity.*—Rounded to slightly elongated in suture plane. Average depth — ⅜ inch. Average breadth — ½ inch.

Stem:

*Size.*—Medium. Average length — ½ inch. Average width — 1/16 inch.

*Color.*—Linden green to olive yellow (2-C-5) to (2-D-8).

Flesh:

*Ripens.*—Nearly uniform, only slightly earlier near apex.

*Texture.*—Firm, meaty.

*Fibers.*—Few, small, tender.

*Firmness.*—Good, comparable to 'Flavorosa'.

*Aroma.*—Slight.

*Amydgalin.*—Undetected.

*Eating quality.*—Very good.

*Flavor.*—Very good, sweet, good balance between acid and sugar.

*Juice.*—Moderate, enhances flavor.

*Brix.*—15.5° soluble solids. Varies with amount of fruit per tree, climatic and soil conditions.

*Color.*—Cerise to ruby red (12-C-8) to (12-D-8), some slight pale yellow bleeding into flesh around pit cavity. Pit cavity color — dark ruby (12-E-8).

Skin:

*Color.*—Light yellow to yellow (4-A-5) to (4-A-7) ground color. Overspread with violet brown to brownish violet (10-F-8) to (11-E-8). Very small, randomly spaced areas of ground color showing at skin surface giving speckling pattern.

*Thickness.*—Medium, minimal scarring or discoloring during picking and packing trials.

*Surface texture.*—Smooth.

*Bloom.*—Moderate, complete coverage.

*Tendency to crack.*—None.

*Tenacity.*—Tenacious to flesh.

*Astringency.*—None.

Stone:

*Type.*—Clingstone.

*Size.*—Large. Average length 1 inch. Average width ¾ inch. Average thickness ⅜ inch.

*Form.*—Obovoid.

*Base.*—Usually flat, varies from flat to rounded.

*Apex.*—Cuspidate. Average length — 3/32 inch.

*Surface.*—Lightly pitted throughout. Several small ridges extending from base approximately ½ distance toward apex. One long groove on each side of suture extending from base to apex.

*Sides.*—Varies from equal to unequal with one side extending further from suture plane.

*Tendency to split.*—None.

*Color.*—Varies from tan to light brown (5-B-4) to (5-B-6) when dry.

Use: Dessert. Market — local and long distance.

Storage quality: Good, held 3 weeks in cold storage at 38° to 42° F. without internal breakdown of flesh or appreciable loss of flavor or eating quality.

Shipping quality: Good, picking, packing and transporting of fruit gave minimal bruising of flesh or skin scarring during shipping trials.

Disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics, with abnormal fungus, bacterial, virus or insect susceptibiity is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its large size, vigorous, upright growth and being a productive and regular bearer of large, clingstone, red flesh fruit with very good flavor and eating quality; and, in comparison to the interspecific tree 'Flavorosa' (U.S. Plant Pat. No. 10,285), the new tree blooms one week later in the spring, produces fruit that is more round in shape and is 7 to 10 days later in maturity.

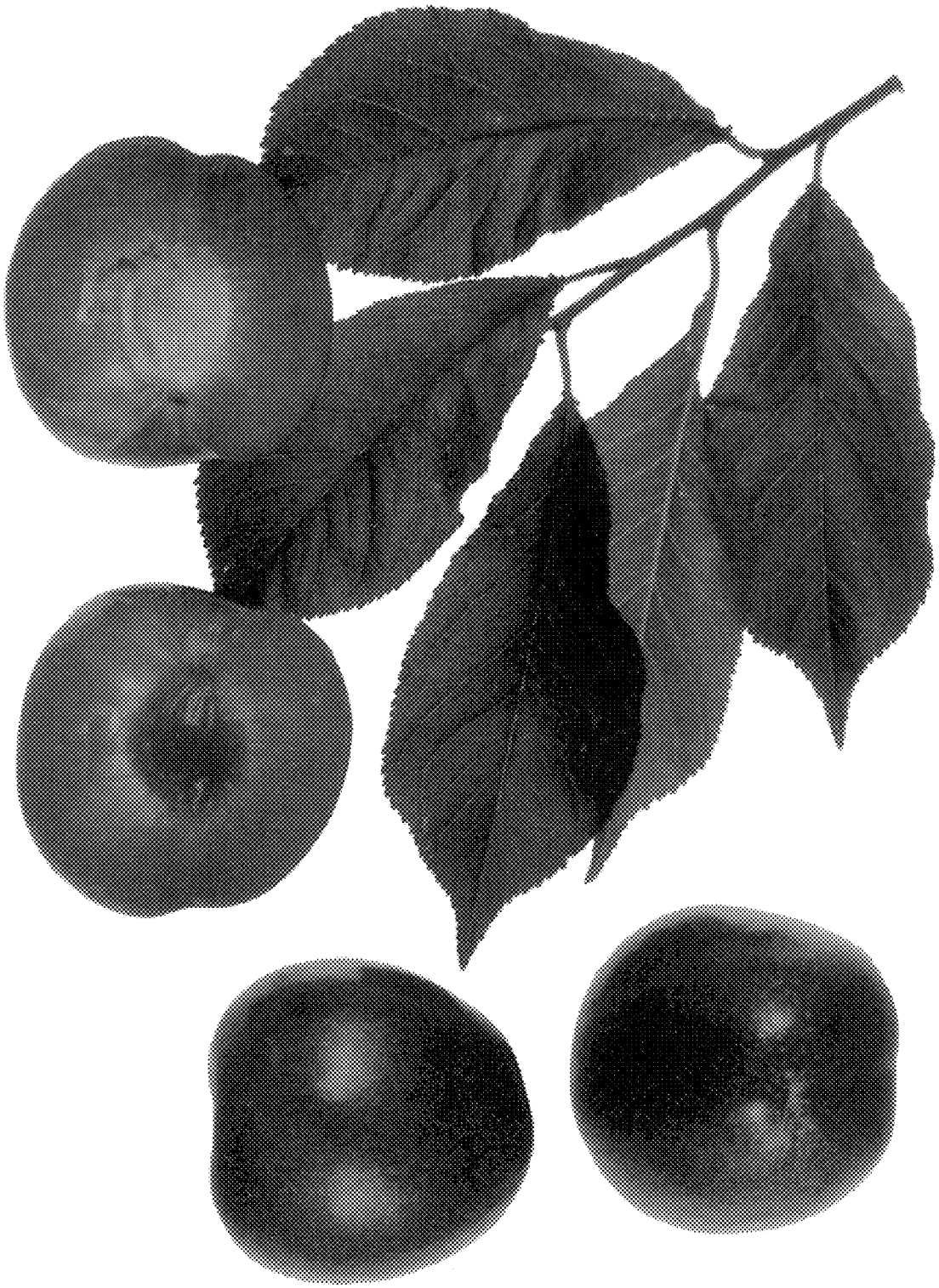

* * * * *